US00PP34620P2

(12) United States Plant Patent
Wheeler et al.

(10) Patent No.: US PP34,620 P2
(45) Date of Patent: Oct. 4, 2022

(54) BLUEBERRY PLANT NAMED 'BB14-321NA-1'

(50) Latin Name: *Vaccinium corymbosum*
Varietal Denomination: BB14-321NA-1

(71) Applicant: BB IP Repository, LLC, Grand Junction, MI (US)

(72) Inventors: Edmund J. Wheeler, Holland, MI (US); Maria Pilar Banados, Santiago (CL)

(73) Assignee: BB IP Repository, LLC, Grand Junction, MI (US)

( * ) Notice: Subject to any disclaimer, the term of this patent is extended or adjusted under 35 U.S.C. 154(b) by 0 days.

(21) Appl. No.: 17/714,374

(22) Filed: Apr. 6, 2022

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
See application file for complete search history.

*Primary Examiner* — Annette H Para
(74) *Attorney, Agent, or Firm* — King IP Law; Joshua King

(57) ABSTRACT

'BB14-321NA-1' is the first known genotype selected in a low-chill temperate environment of Central Chile and tested also in the tropical environment of Peru. 'BB14-321NA-1' is a high-yielding early season variety that can break buds and produce fruit with very low chill or no-chill since it does not develop endo-dormancy. The fruit of 'BB14-321NA-1' is very large with medium blue color, high bloom and excellent fruit appearance. Fruit is firm and has juicy texture. The eating quality of 'BB14-321NA-1' is very good, and 'BB14-321NA-1' appears to have the option of jumbo early fruit for early spring production in many places of the world. It can be cultivated in soil and soilless production systems.

18 Drawing Sheets

Latin name: *Vaccinium corymbosum.*
Common name: Blueberry.
Cultivar name: 'BB14-321NA-1'.

BACKGROUND AND SUMMARY

Blueberries are a well-known fruit enjoyed by many throughout the world. The novel blueberry variety in this application, 'BB14-321NA-1', is the first genotype from Berry Blue BBIP Genetics selected at the low-chill temperate environment of Nancagua Region of the O'Higgins (34° 43'58,89" S; 71° 10' 24,75"O) in Chile.

One example of an existing known blueberry variety is 'Kestrel' FL02-40 (U.S. Plant Pat. No. 21,719). Compared to 'Kestrel', 'BB14-321NA-1' has more vigor, it has earlier fruit in the season and has much larger fruit. The fruit of 'BB14-321NA-1' is large and well presented on the plant and is produced in one-year old shoots (in Chile) and in current season shoots (in Peru under tropical environment).

Comparing 'BB14-321NA-1' to 'Stellar' (brand name for 'BB06-50FL-1', U.S. Plant Pat. No. 30,445), the immature summer cane color 'BB14-321NA-1' is yellow green, compared to olive green in Stellar; the fruit of 'BB14-321NA-1' is earlier and more acidic, and flatter compared to 'Stellar'. The mature leaves of 'BB14-321NA-1' are larger and more elongated than in Stellar and also it has a shorter leaf petiole.

Additional examples of an existing, patented blueberry variety are 'Rocio', U.S. Plant Pat. No. 20,374, 'Kestrel' (brand name for FL02-40, U.S. Plant Pat. No. 21,719) and 'Stellar'. Compared with these varieties in Chile, 'BB14-321NA-1' has the largest fruit and the least levels of sugars (o Brix) as shown in Table 1, which provides fruit characteristics of 'BB14-321NA-1' compared to other commercial varieties grown in Chile.

Table 1. Fruit characteristics of 'BB14-321NA-1' compared to other commercial varieties grown at the same location in Nancagua, Region of O'Higgins in Chile 2020.

| Variety | Fruit weight (g) | Fruit diameter (mm) | Fruit firmness Baxlo shore | Soluble solids (Brix) | ACIDEZ TITUL-ABLE (%) | Ratio (SS/ acid) |
|---|---|---|---|---|---|---|
| KESTREL | 2.5 | 17.6 | 78 | 14.2 | 0.48 | 29.6 |
| STELLAR | 3.4 | 18.7 | 76 | 12.4 | 0.5 | 24.8 |
| ROCIO | 2.8 | 18.0 | 80 | 13.6 | 0.68 | 20.0 |
| BB14-321NA-1 | 4.1 | 20.7 | 79 | 11.7 | 0.61 | 19.2 |

The present cultivar, 'BB14-321NA-1', provides one or more advantages compared to these and/or other blueberry varieties.

The fruit of 'BB14-321NA-1' is large and medium blue violet color, with excellent firmness and very juicy texture. The eating quality of 'BB14-321NA-1' is excellent, having a sugar/acidity balance of 20. 'BB14-321NA-1' is a highly productive variety with early maturity fruit and very good fresh market quality. Time of fruit production in 'BB14-321NA-1' in Chile is regulated by the Growing Degree days accumulated at the end of the winter and early spring, and in Peru it can be regulated by the pruning date and environment conditions. This is another distinct characteristic of 'BB14-321NA-1' that can be adapted to both environments. 'BB14-321NA-1' was selected under substrate soilless production and under high tunnel cultivation system.

Areas of adaptation of 'BB14-321NA-1' include temperate low-chill areas of Chile, US, Europe or Asia, and also tropical areas like the coast of Peru, Ecuador, and Colombia and other tropical areas with no-winter chill. 'B3B14-321NA-1' has been tested in the low-chill area of Nancagua in soilless production under tunnel and in the no-chill environment in Chao, Peru under soil and soilless production.

Plants of 'BB14-321NA-1' are medium upright with a small size crown 'BB14-321NA-1' produces many upright canes, with high apical dominance.

The fruit of 'BB14-321NA-1' is large to extra-large, moderately sweet with medium acidity, high bloom, and firm berries with a small and dry scar. 'BB14-321NA-1' is ideal for fresh market and shows a fruit storability of about 3 to 4 weeks. The productivity of 'BB14-321NA-1' is similar to 'Rocio' and higher than 'Kestrel' in Chile although it has yet not been tested commercially yet The flowering period of 'B3B14-321NA-1' is earlier than 'Kestrel' or 'Rocio' in the same low-chill environment of Chile and it start at the end of May in vertical shoots. In Peru flowering of 'BB14-321NA-1' starts 90 to 95 days after pruning, which is shorter than 'Scintilla' (U.S. Plant Pat. No. 19,233) and 'Ventura', which take about 120 to 150 days. The fruiting period of 'BB14-321NA-1'3' is earlier than 'Kestrel' and 'Rocio', starting at the end of August in Chile and 180 to 185 days after pruning in Peru.

BRIEF DESCRIPTION OF THE PHOTOGRAPHS

DETAILED DESCRIPTION

Figure 1A:
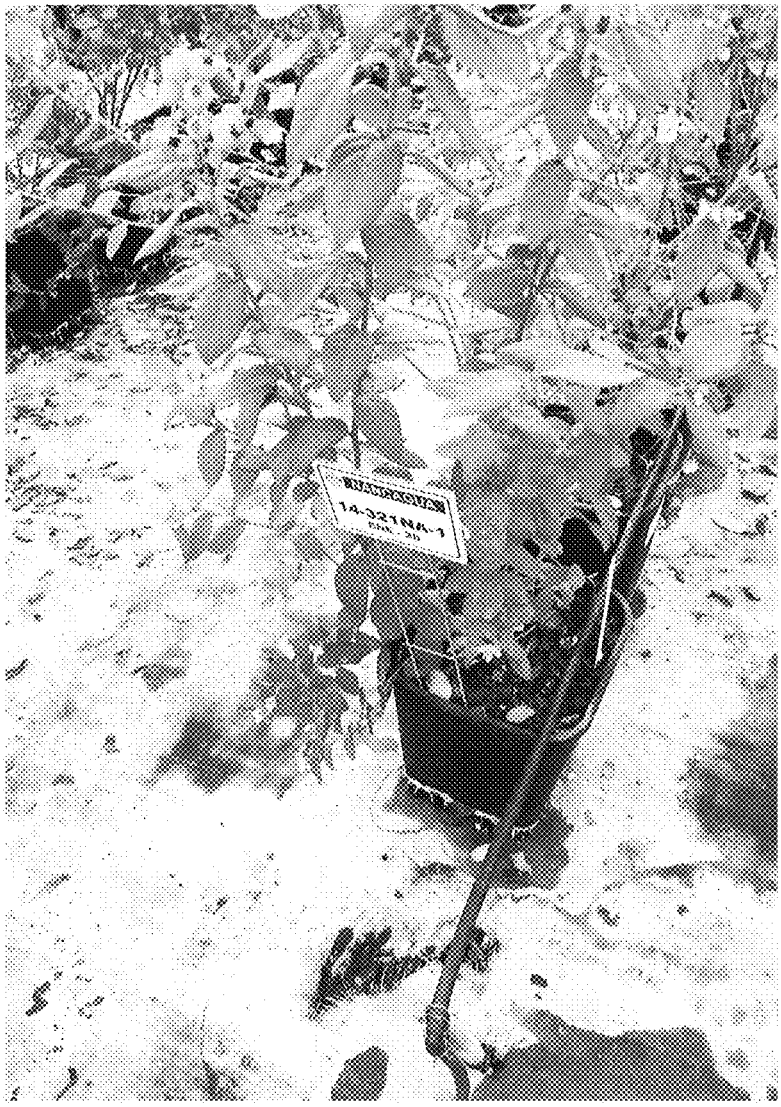
FIGS. 1A and 1B are photographs of BB14-321NA-1 grown in containers in Nancagua, Chile in June 2021 showing the growth habit and plant structure.
Figure 1B:
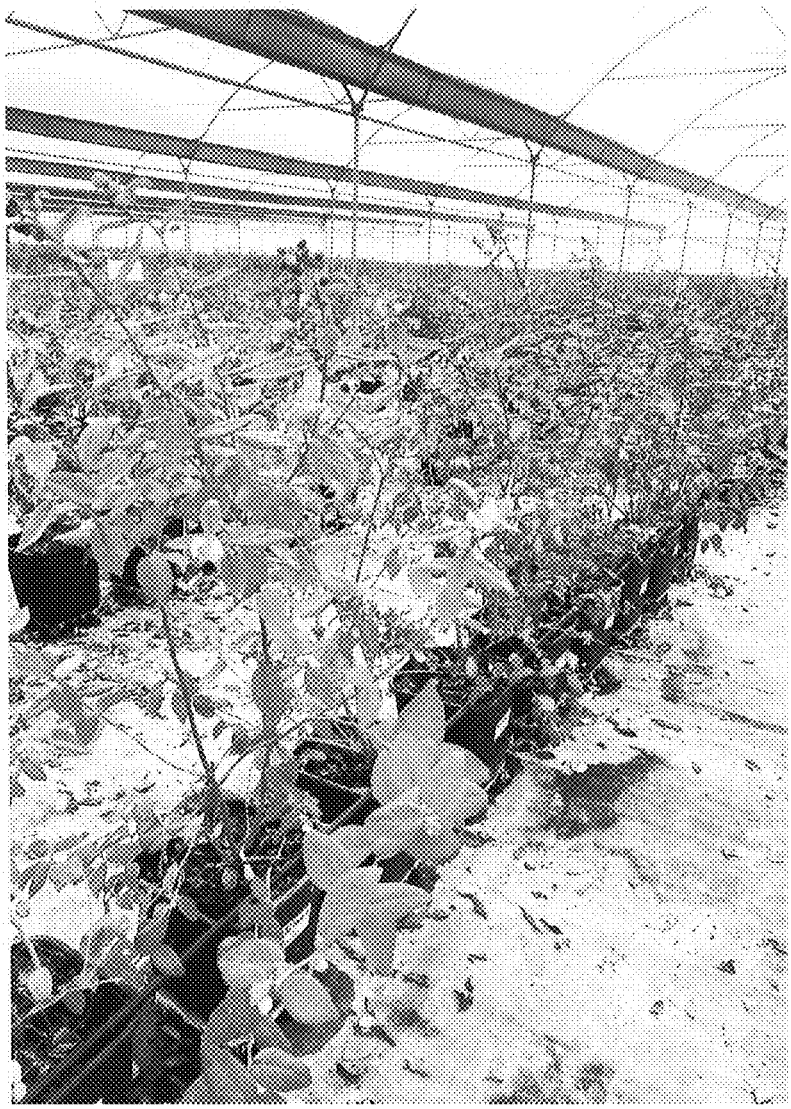

Note: statements of characteristics herein represent exemplary observations of the cultivar performance in Nancagua, Chile (34° 43'58,89" S; 71° 10' 24,75"O) and in Chao, Peru (8° 35'12"S 78° 35'58"W) and might have some phenotypic variations depending on time of year, location, annual temperature conditions and weather, etc. Where dimensions, sizes, colors, and other characteristics are given, it is to be understood that such characteristics are approximations and averages. The descriptions reported herein are based on the original selected individual bush observed in successive years through 2017, 2018, 2019, and 2020 in fields near Nancagua, Chile and in cloned propagated plants planted at the same place in Nancagua in 2019 and also in Chao, Peru in 2019 and 2020. Laboratory analysis of fruit characteristics were done in Nancagua and in Chao, Peru.

Cultivar Name: 'BB14-321NA-1'

Classification:

Family: Ericaceae.

Botanical name: *Vaccinium corymbosum*

Common name: Blueberry.

Parentage:

Female Parent

Name: 'Raven' U.S. Plant Pat. No. 21,374 (child of 'FL01-26' (unpatented) and 'Windsor' (U.S. Plant Pat. No. 12,783).

U.S. Plant Patent: U.S. Plant Pat. No. 21,374 Oct. 12, 2010

Compared to 'Raven', 'BB14-321NA-1' produces fruit on current season shoots in the tropical environment of Peru, and in one-year old shoots in the low-chill area of Nancagua. They both have large fruit, however 'BB14-321NA-1' produced fruit much earlier than 'Raven' and 'BB14-321NA-1' does not require chill hours to break buds, since flowers are present even at the end of the fall in Nancagua, Chile. 'BB14-321NA-1' also produced high yields in the no-chill environment of Chao, Peru.

Male Parent

Name: 'BB05-225FL-1' (child of Emerald (U.S. Plant Pat. No. 12,165) x Jewel (U.S. Plant Pat. No. 11,807).

U.S. Plant Patent: Unpatented.

Compared to 'BB05-225FL-1', the fruit of 'BB14-321NA-1' is larger, earlier and firmer. They both produce fruit on one-year old shoots in temperate environments.

'BB14-321NA-1' originated as a seedling selected from a cross of 'Raven' and 'BB05-225FL-1' made in a greenhouse in Grand Junction, Mich. in 2014. Seed was germinated in Chile and plants of that cross were grown and planted in a seedling evaluation site in Nancagua, Region de O'Higgins in Chile in a soilless system under tunnel in November 2016 and evaluated for two years in 2017 and 2018. The plant was first selected on Nov. 16, 2017, based on its excellent fruit characteristics such as being jumbo, sweet and firm both in the field and after 5 days cold storage. The selection was given the number 'BB14-321NA-1'. It was tested under this number for two years. The individual bush of 'BB14-321NA-1' was observed and evaluated for productivity and fruit quality in the same site for two successive years through 2017 and 2018. Current-season shoot samples of the mother plant were taken in 2018 for in vitro clonal propagation in Chile. Clonal plants were planted in an advanced trial in a soilless system near Nancagua, Chile and sent to Chao Peru in 2019 and the fruit was evaluated. All of the observed bushes have retained the characteristics of the original selection in Chile, and showed some phenotypic variation in Peru, such as more acidic fruit.

'BB14-321NA-1' has been asexually propagated via tissue-cultured micro shoots since 2018 and dozens of individual shoots have been rooted in Chile and in Chao, Peru. Propagated plants have been under evaluation since October 2019.

General Description of 'BB14-321NA-1'

'BB14-321NA-1' is a new and distinct low-chill tetraploid Southern highbush blueberry variety (*Vaccinium*) of complex ancestry, based largely on *V. corymbosum* and *V. darrowii*, from the breeding program of Berry Blue, LLC. 'BB14-321NA-1' is a very productive early-season variety with high quality fresh market characteristics. 'BB14-321NA-1' has a good upright bush and a small sized crown with erect new canes and a high apical dominance. The bush has a very good vigor, and 'BB14-321NA-1' has shown very good adaptability to sandy soil and substrate mix of coco fiber and peat. The fruit itself is medium blue violet color, with good firmness and very juicy texture. The fruit appearance is excellent due to its large size and high bloom. Fruit should be picked on a regular schedule about 7 to 10 days to maintain the quality of the fruit and allow for flavor and sugar development. 'BB14-321NA-1' is expected to be released as the first cultivar selected in low-chill central Chile and as an improvement over 'Rocio' and 'Kestrel' in terms of fruits size and earliness.

References to color refer to The Royal Horticultural Society Colour Chart 2007 Fifth Edition.

Morphological characteristics reference: Plant Systematics, Jones and Luchsinger, 2 Ed., McGraw Hill, New York, ISBN 0-07-032796-3, 1986.

Device used to measure Soluble Solids (SS-Brix°), Titratable acidity (TA), pH: PAL-BX/Acid 7, Atago USA, Inc., Bellevue, Wash.

Firmness readings: Shore by BAXLO Durometer (Olmos, Peru).

Sugar and acidity measurements, ATAGO (Olmos, Peru)

General Description: medium upright with a small size crown; moderately sweet, medium acid, firm and crunchy berry adapted to a low-chill and no-chill environment. 'BB14-321NA-1' blooms about 90 days after pruning in Peru, and from mid-May to July in the temperate area of Nancagua, Chile. The average 50% ripening date is 280 days after pruning in Peru, and in early October in Chile. Firmness ranges from 70 to 78 Baxlo Shore, Brix° from 10 to 12% and titratable acidity from 0.6 to 0.8% (Table 1) and a sugar to acid ratio of 18 to 20 in Chile. Storability is medium and it could last up to 25 days in cold storage.

Figure 2A:
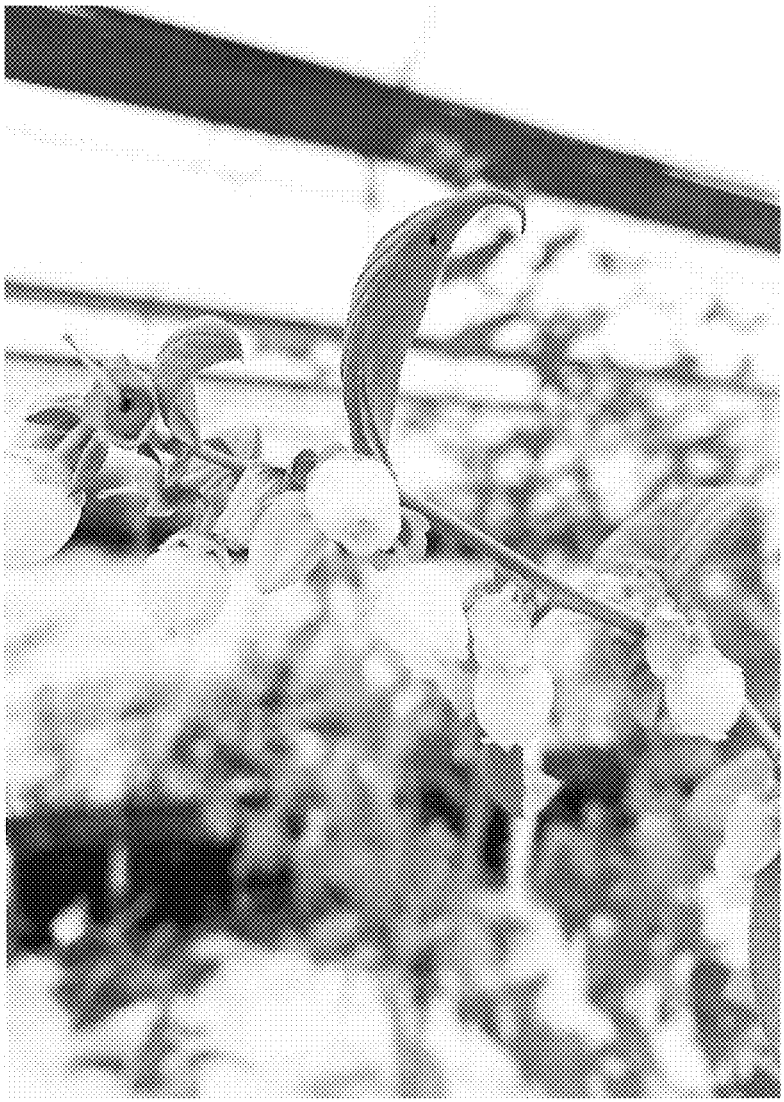
FIGS. 2A-2D are photographs of BB14-321NA-1 flowers clusters in 1 year-old shoots. Nancagua, Chile June 2021.
Figure 2B:
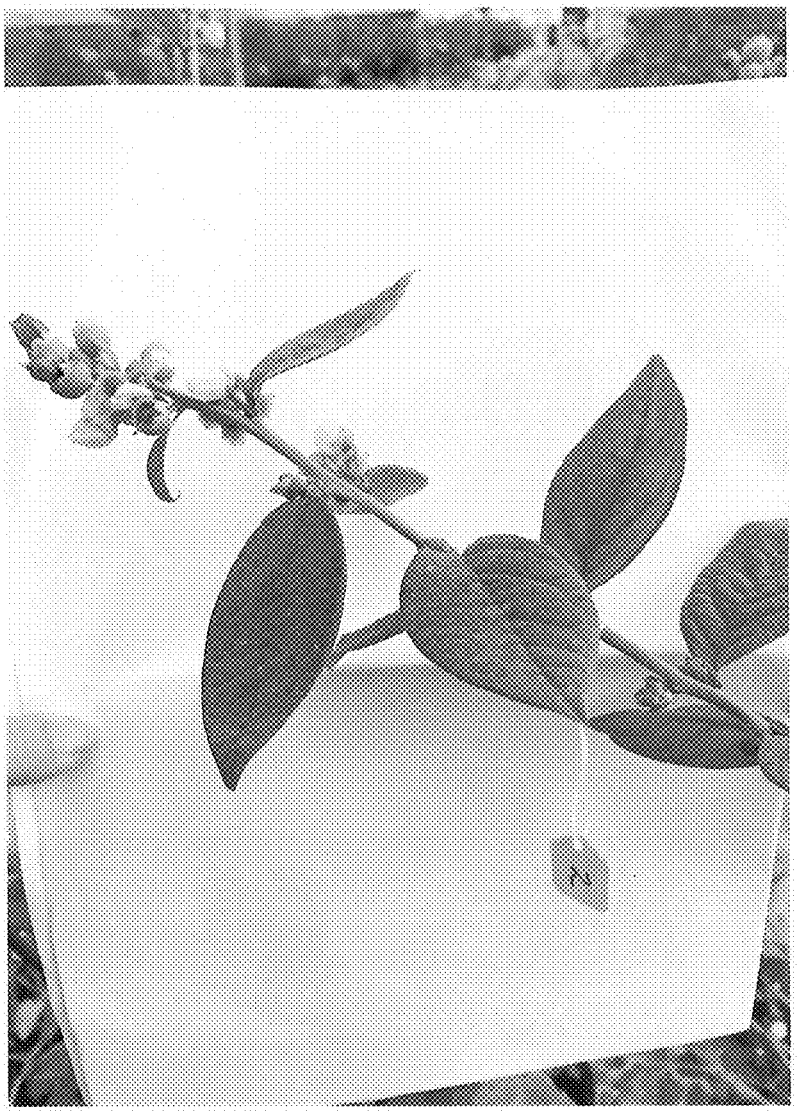
Figure 2C:
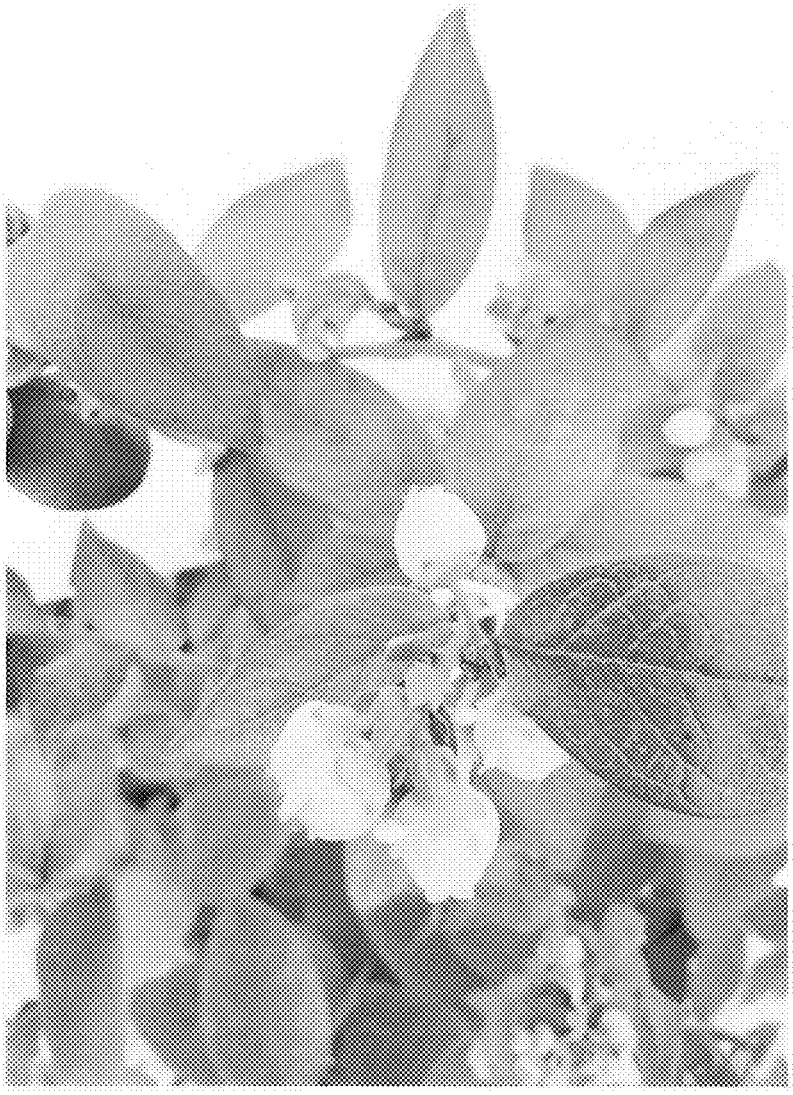
Figure 2D:
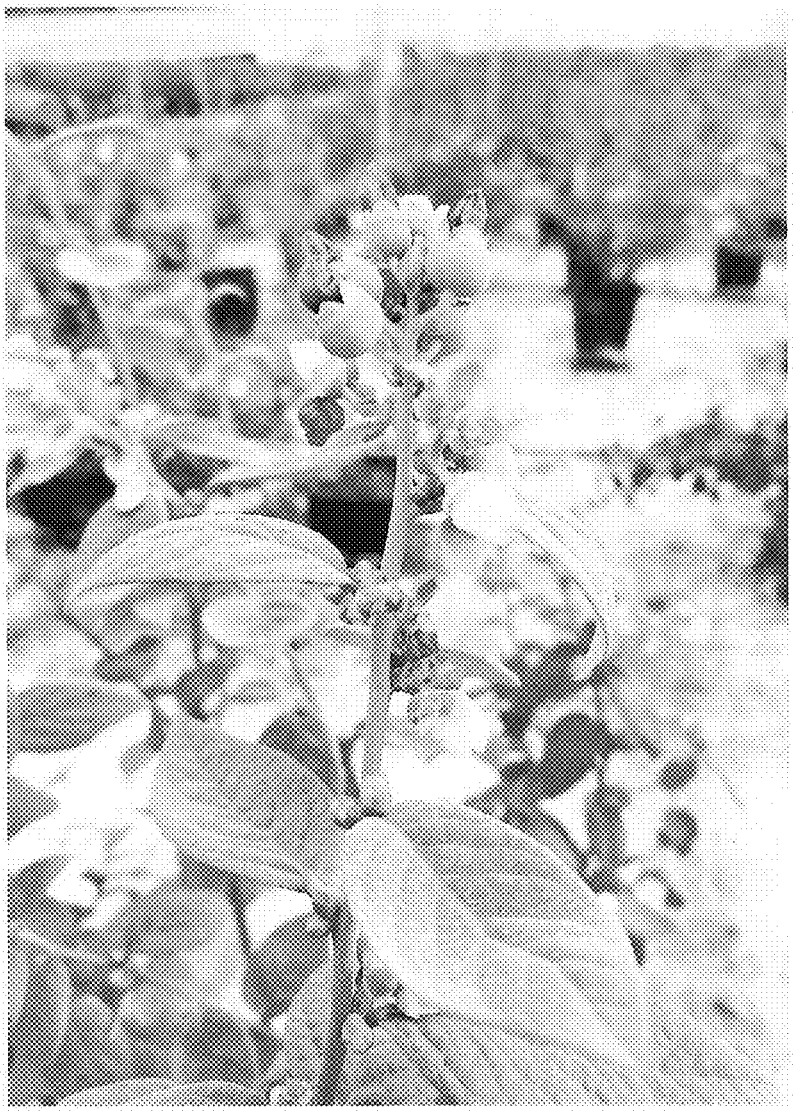
Figure 3A:
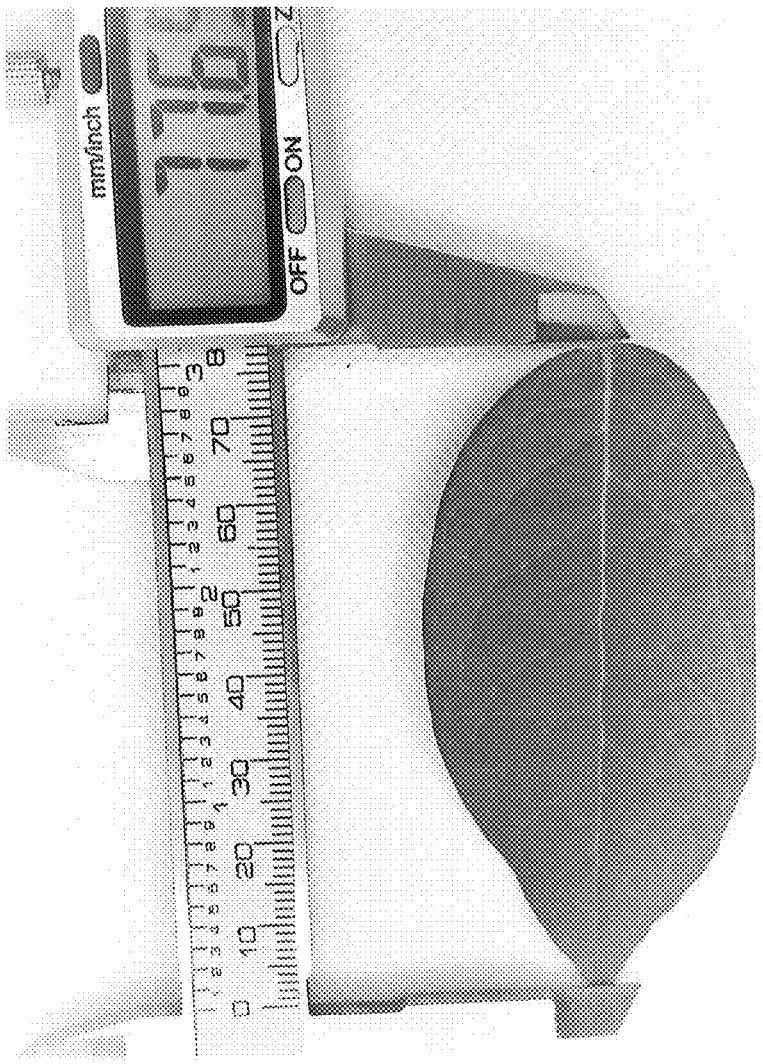
FIGS. 3A-3E are photographs of BB14-321NA-1 mature leaves showing size and color. Nancagua, Chile, November 2021.
Figure 3B:
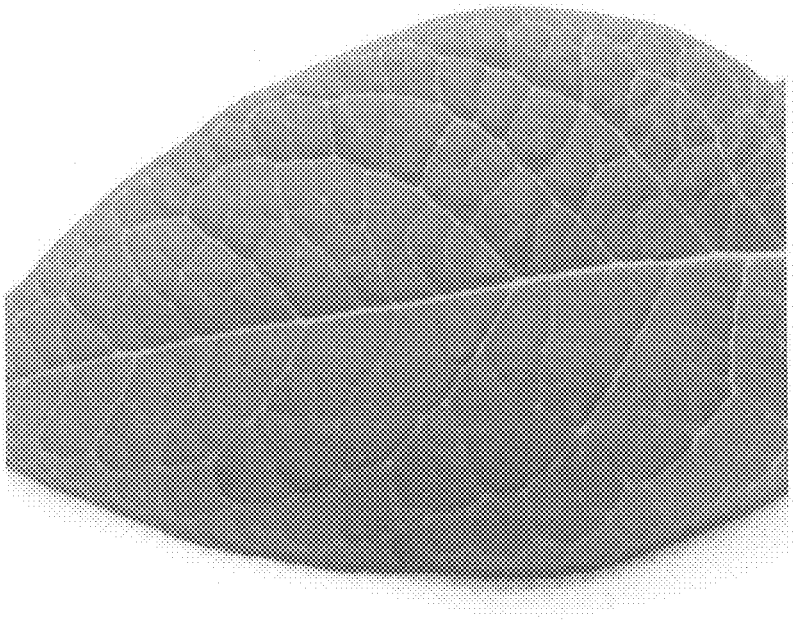
Figure 3C:
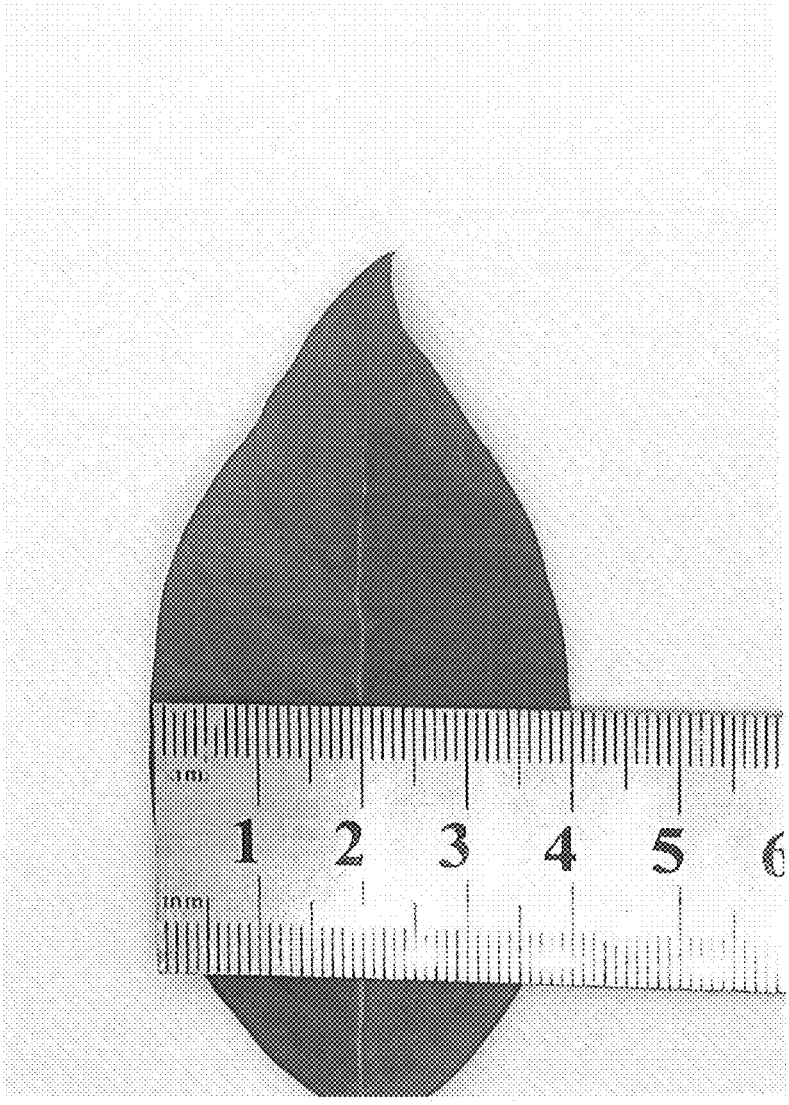
Figure 3D:
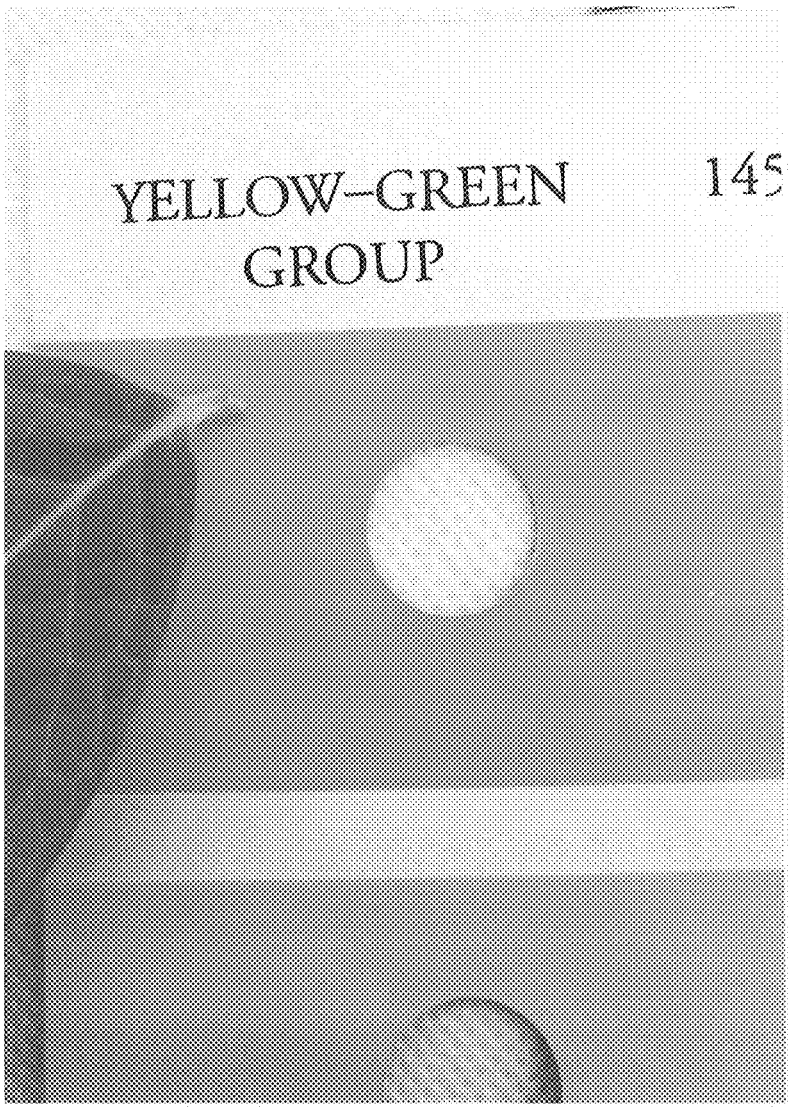
Figure 3E:
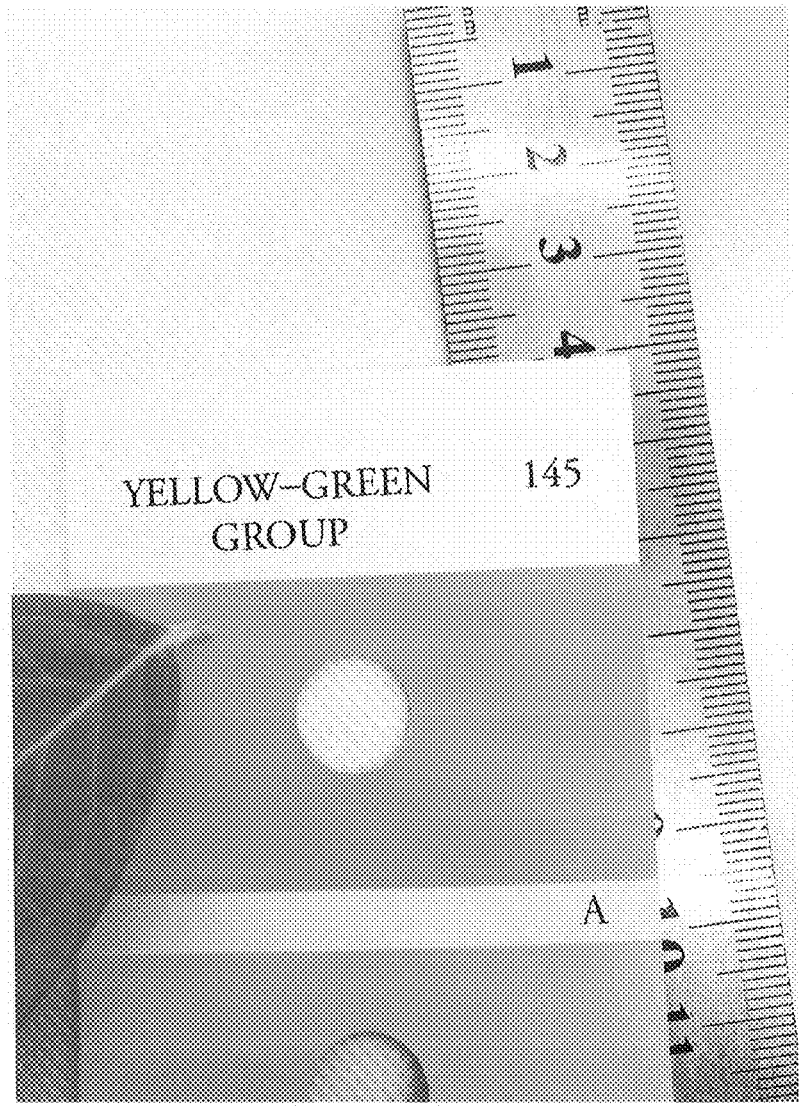

Specific features of the variety:

Plant:

*Growth habit.*—Upright.
*Plant width.*—80 cm at mid-bush height.
*Plant height.*—120 cm.
*Productivity.*—1.9 kg per plant at year 2.
*Cold hardiness/tolerance.*—Not tested.
*Chilling requirement.*—This is no to low-chill highbush blueberry plant, it has a normal bud break in a low chill (200-400 Chill hour) environment as well as a no-chill environment of Peru. This is probably due to differences in the dormancy statues establish at the different latitudes.
*Canes.*—Moderately branched, average 5 to 6 shoots per bush, average 80-90 cm length, medium number of laterals.
*Young current-season-shoots.*—Yellow-Green Group 145A and B (FIG. 2A).
*One-year-old shoot branches color.*—Yellow-Green Group 144C. Texture is soft.
*Mature cane color.*—Yellow green group N146 C.
*Mature cane texture.*—Medium rough.
*Fruiting wood.*—One-year old shoot and current season shoots.
*Internode length range.*—1.8 to 3.2 cm.
*Surface texture of new wood.*—Smooth.
*Time of beginning of leaf bud burst.*—Bud break of vegetative buds occurs on July 20 in Nancagua, Chile (South hemisphere).
*Time of beginning of flowering.*—May 1$^{st}$, in Nancagua, Chile.
*Date of 50% open flowers.*—July 15 in Nancagua, Chile.
*Time of beginning of fruit ripening.*—Fruit ripening begins on August 20 in Nancagua under tunnel production.
*Disease resistance/susceptibility.*—None claimed.
*Young current-season-shoots.*—Yellow-Green Group 144D.
*One-year-old short branches color.*—Yellow-Green Group 145B. Texture is soft.

Foliage:

*Young, newly expanded leaf color.*—Upper surface: Yellow-Green Group 146B; Lower surface: Green Group 139C.
*Leaf arrangement.*—Simple Alternate.
*Mature, fully expanded leaves.*—Upper surface: Green 146B; Lower surface: Green 139C.
*Leaf margins.*—Entire.
*Leaf venation.*—Pinnate.
*Leaf shape.*—Ovate.
*Leaf length.*—75 mm to 80 mm, average 78 mm.
*Leaf width.*—35 mm to 42 mm, average 40 mm.
*Leaf color.*—Green Group 146 B.
*Leaf apices.*—Acuminate.
*Leaf bases.*—Acute.
*Vein and petiole coloration.*—Green Group, 145AB.
*Petiole length.*—2 to 3 mm.
*Petiole diameter.*—2 mm.
*Evergreen.*—this variety is evergreen and keep part of their leaves during fall and winter.
*Fall leaf color.*—Does not apply for this genotype.

Leaf dimensions:

*Overall shape.*—Medium Obtuse.
*Length.*—75 to 80 mm, Average 78 mm.
*Width.*—35 to 42 mm, Average 40 mm.
*Leaf margins.*—Entire, no visible (microscope 10×) pubescence and a few nectaries.
*Leaf surface.*—Smooth upper and lower, no visible (microscope 20×) pubescence.

Figure 4A:
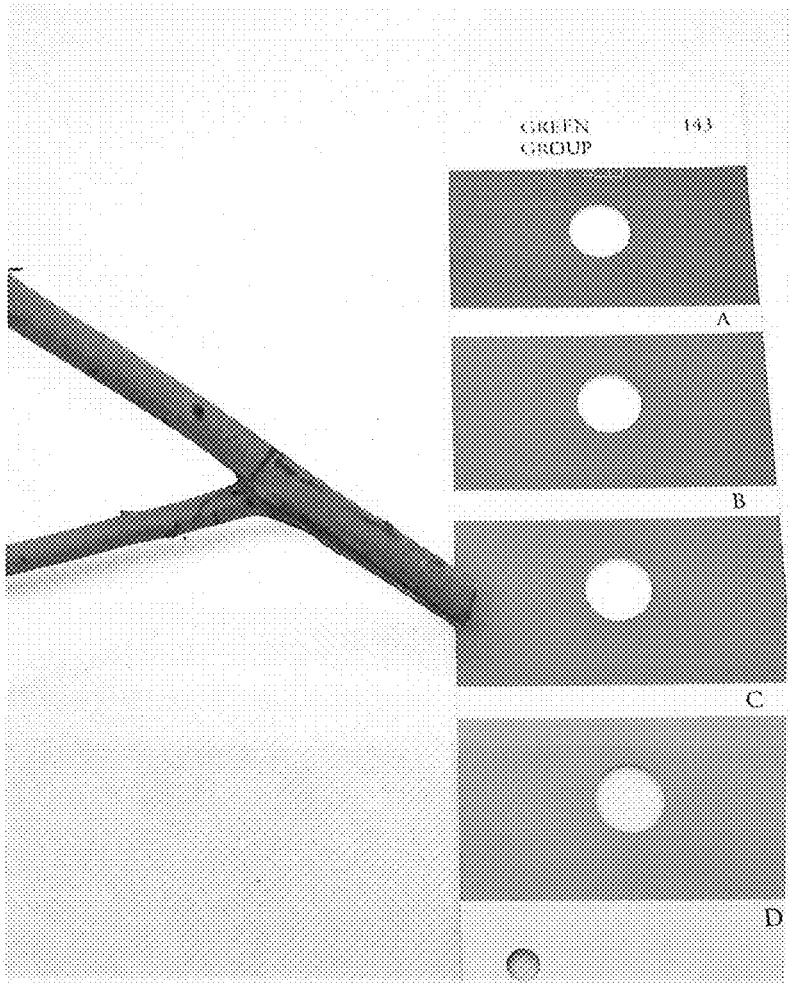
FIGS. 4A-4C are photographs of BB14-321NA-1 showing the color of mature and young shoots.
Figure 4B:
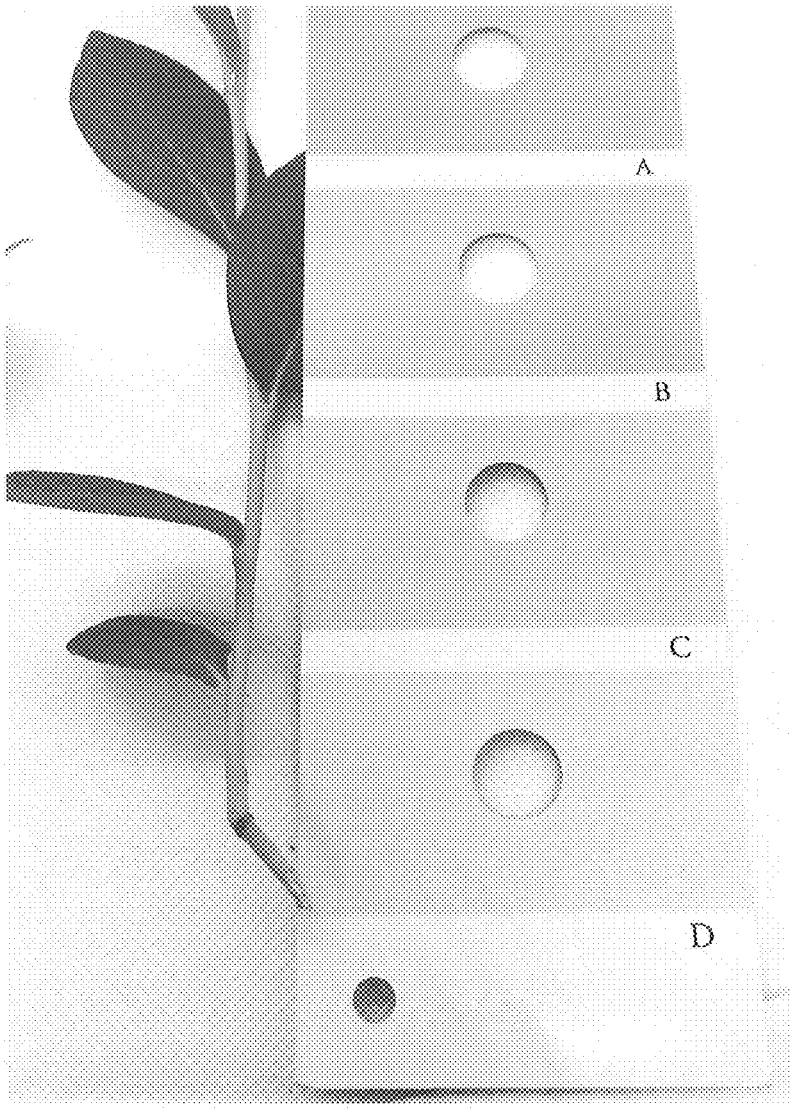
Figure 4C:
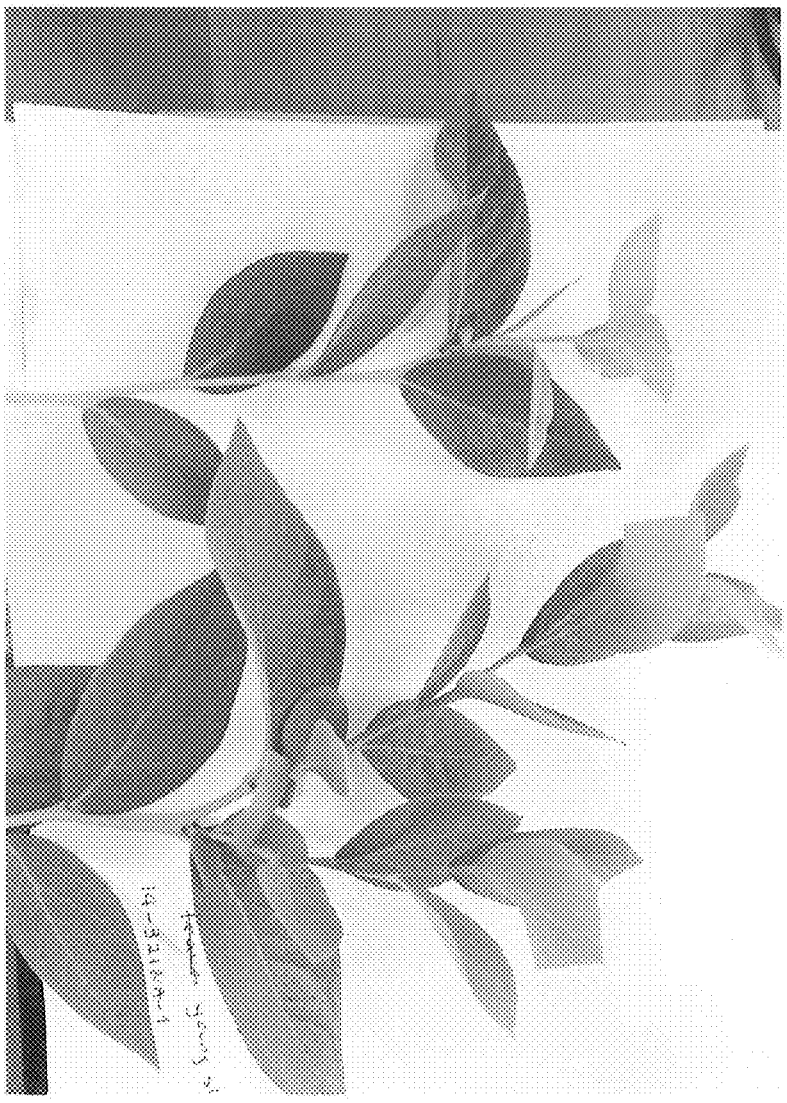
Figure 5A:
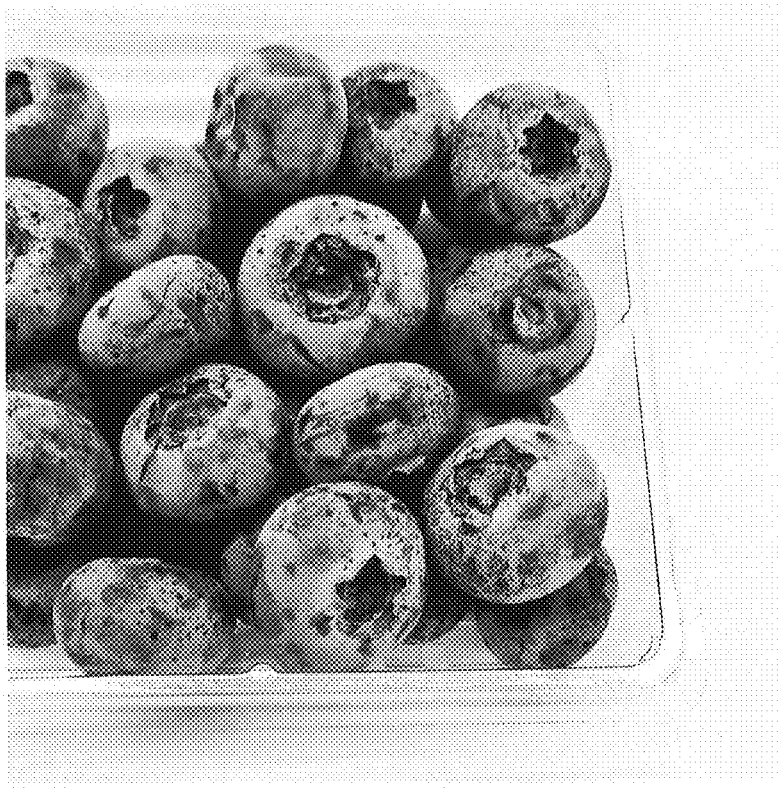
FIGS. 5A-5D are photographs of BB14-321NA-1 showing mature fruit color, size and height.
Figure 5B:
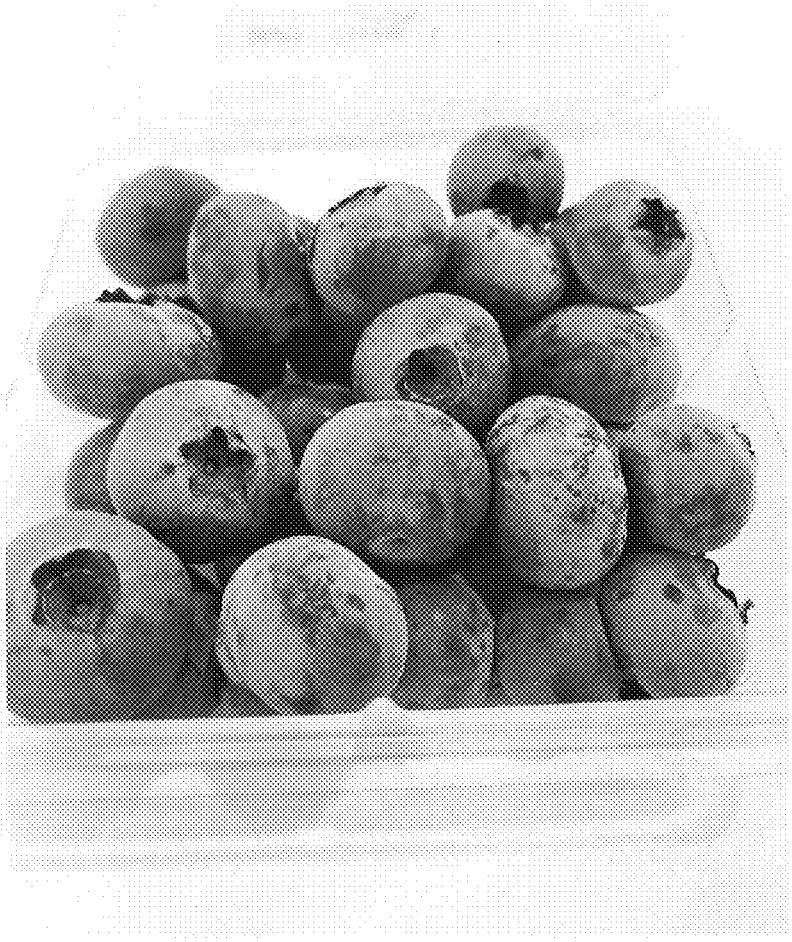
Figure 5C:
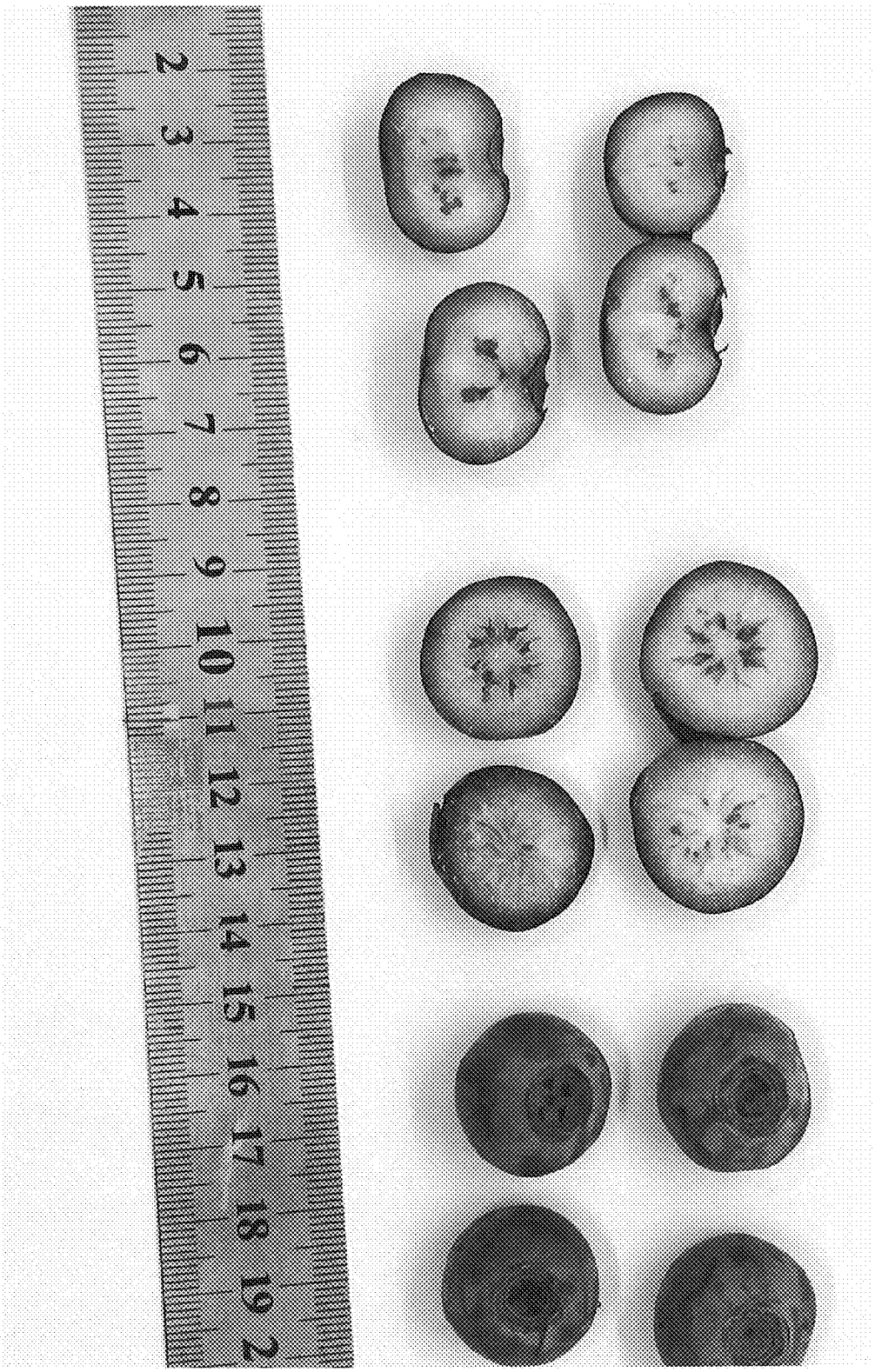
Figure 5D:
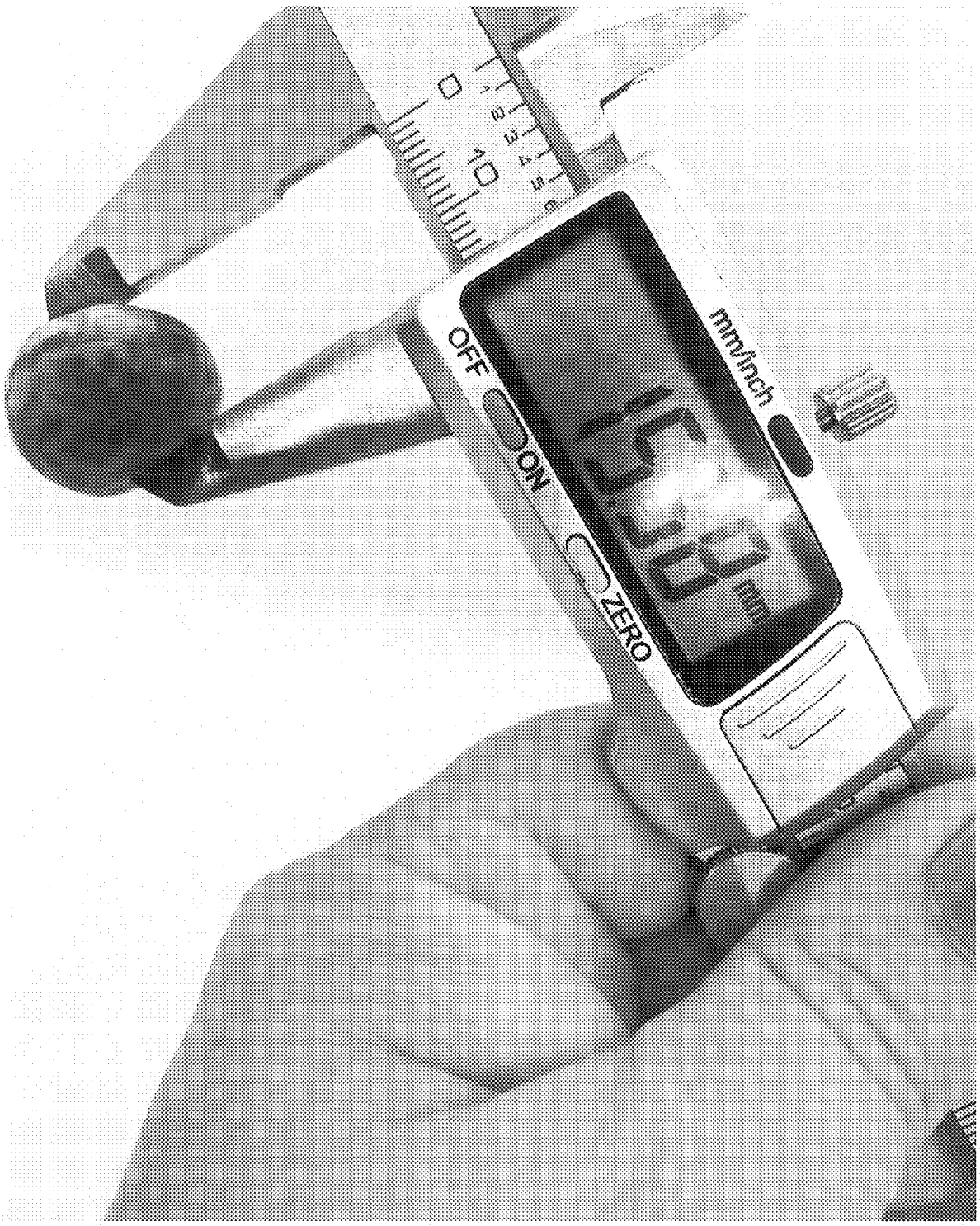

Leaf buds:

*Shape.*—Elongated.
*Length.*—2 to 3 mm.
*Width.*—1.6 mm.
*Color.*—Yellow Green Group 145C+greyed purple group 184B (FIG. 4).

Flower buds:

*Shape.*—Round.
*Length.*—5 to 8 mm.
*Width.*—5 to 6 mm.
*Color.*—Greyed purple group 184AB.

Flower:

*Flower shape.*—Medium urceolate.
*Flower bud number per lateral.*—8 to 12.
*Flowers per bud.*—3 to 6.
*Flower fragrance.*—Light floral.
*Corolla color.*—White Group 155B.
*Corolla length.*—6 to 7 mm.
*Corolla width.*—5.5 mm.
*Corolla aperture width.*—3 mm.
*Corolla texture.*—Smooth.
*Flower peduncle length.*—7 to 8 mm.
*Peduncle diameter.*—1 mm Peduncle.
*Texture.*—Smooth.
*Peduncle color.*—Green Group 145B.
*Flower pedicel length.*—8 mm.
*Pedicel diameter.*—4 mm.
*Pedicel texture.*—Smooth.
*Pedicel color.*—Green Group 146D.
*Calyx (with sepals).*—5 mm.
*Calyx color.*—Green Group 143 B.
*Stamen length.*—5 to 6 mm.
*Stamen number per flower.*—10.
*Stamen filament color.*—Greyed Orange Group 163A.
*Style.*—5.4 mm, top of ovary to stigma tip.
*Style color.*—Green group 143A. Pistil extends over the top of corolla 1 mm.
*Ovary color.*—Medium Green 145B.
*Anther length.*—3.8 to 4.5 mm.
*Number.*—1.
*Anther color.*—Greyed-Orange group 163A.

Pollen:

*Abundance*.—Medium.

*Color*.—Yellow 10D.

Fruit:

*Date of 50% maturity*.—Mid October in Nancagua, 280 days after pruning in Chao, Peru

*Duration of ripening*.—4 months in Nancagua, Chile and up to 7 months in Chao, Peru.

*Yield*.—1.9 kg per plant in Chile and 3.5 kg/plant in Peru in year 2.

*Cluster density*.—Loose.

*Immature fruit color*.—Green Group N 143B.

*Berry color with wax*.—Violet Group 98D.

*Berry color with wax removed*.—Blue Group 103A.

*Berry flesh color*.—Green white Group 157BCD.

*Berry surface wax abundance*.—Heavy.

*Berry weight*.—3.4 to 6 grams/berry.

*Berry size diameter*.—20.8 to 24 mm.

*Berry height*.—13 to 16 mm, average 15.5 mm.

*Berry width*.—22 mm.

*Aspect* (*h/w*).—0.68.

*Berry shape*.—Oblate.

*Average number of fruits per cluster*.—4 to 6.

*Detachment force*.—Medium.

*Self-fruitfulness*.—Fair, cross pollination may be desirable for maximum yield and fruit size.

*Fruit stem scar*.—2 to 3 mm diameter, 2 mm depth.

*Calyx*.—5 point.

*Calyx diameter*.—10 to 12 mm.

*Calyx depth*.—2.50 mm.

*Berry firmness*.—Firm, 75 to 78 Shore of Baxlo.

*Berry sweetness*.—Brix°=10 to 12.

*Berry acidity*.—Titratable acidity=0.6% to 0.8%.

*Berry flavor and texture*.—Good blueberry flavor, balanced sugar and acidity.

*Storage ability*.—Medium high, 3-4 weeks in refrigerated storage.

*Suitability for mechanical harvesting*.—Not tested.

Seed:

*Seed abundance in fruit*.—Medium, 12 to 16 seed per fruit.

*Seed color*.—Grey orange group 172C.

*Seed dry weight*.—7 to 10 mg.

*Seed size*.—0.8 mm length, 0.4 mm width.

Possible typical market uses: Mainly fresh market.

What is claimed is:

1. A new low-chill and tropical highbush blueberry plant cultivar named 'BB14-321NA-1' as described and shown herein.

* * * * *